US008852254B2

(12) United States Patent
Moscovici

(10) Patent No.: US 8,852,254 B2
(45) Date of Patent: Oct. 7, 2014

(54) APPARATUS AND METHOD FOR PROVIDING A MULTI-STAGE LIGHT TREATMENT

(75) Inventor: Lucian Moscovici, Ramat Gan (IL)

(73) Assignee: Lucian Moscovici, Ramat Gan (IL)

( * ) Notice: Subject to any disclaimer, the term of this patent is extended or adjusted under 35 U.S.C. 154(b) by 1737 days.

(21) Appl. No.: 11/884,299

(22) PCT Filed: Feb. 19, 2006

(86) PCT No.: PCT/IL2006/000212
§ 371 (c)(1),
(2), (4) Date: Aug. 14, 2007

(87) PCT Pub. No.: WO2006/087723
PCT Pub. Date: Aug. 24, 2006

(65) Prior Publication Data

US 2008/0103561 A1 May 1, 2008

Related U.S. Application Data

(60) Provisional application No. 60/653,998, filed on Feb. 18, 2005.

(51) Int. Cl.
*A61N 5/06* (2006.01)

(52) U.S. Cl.
USPC .......... 607/88; 607/89; 607/90; 607/91; 607/92; 607/93; 607/94

(58) Field of Classification Search
USPC .................................. 128/898; 607/88–94
See application file for complete search history.

(56) References Cited

U.S. PATENT DOCUMENTS

| 4,858,609 A | 8/1989 | Cole |
| 4,930,504 A | 6/1990 | Diamantopoulos et al. |

(Continued)

FOREIGN PATENT DOCUMENTS

| WO | 2004/110305 | 12/2004 |
| WO | WO 2005/004948 | 1/2005 |

OTHER PUBLICATIONS

"Practice Parameters for the Use of Light Therapy in the Treatment of Sleep Disorders", Chesson et al.; SLEEP, vol. 22, No. 5, 1999.*
World Health Report 1999: Seven leading global health problems estimated by DELY's lost. (The Double Burden: Emerging Epidemics and Persistent Problems) 13-27.

(Continued)

*Primary Examiner* — Ahmed M Farah
*Assistant Examiner* — William Cheng
(74) *Attorney, Agent, or Firm* — Marc Van Dyke; 4$^{th}$ Dimension IP

(57) ABSTRACT

Apparatus and methods for treating psychiatric disorders, mood disorders and circadian rhythm disorders with a multi-stage light protocol are disclosed. The presently disclosed multi-stage light protocol provides a synergistic treatment including up to 4 types of therapies: bright light therapy, extended sleep deprivation therapy, dawn simulation therapy and short to medium wavelength light therapy. According to some embodiments, the first stage of the protocol includes a first time window of 20 minutes during which, for a majority of the time, the light intensity is between 50 lux and 2000 lux. According to some embodiments, the second stage of the protocol includes a second time window of at least 90 minutes during which, for every 10 minute period within the second time window, for a majority of the time, the light intensity is exceeds 100 lux. According to some embodiments, the third stage of the protocol includes a third time window of 60 minutes during which, for a majority of the time, the light intensity exceeds 2000 lux In some embodiments, the light is provided by apparatus including a plurality of LEDs. Typically, the light includes white light having a broad spectrum. In some embodiments, the light further includes light having a medium wavelength, for example, wavelengths between 520 nm and 535 nm.

39 Claims, 4 Drawing Sheets

(56) References Cited

U.S. PATENT DOCUMENTS

| | | | | |
|---|---|---|---|---|
| 5,545,192 | A * | 8/1996 | Czeisler et al. | 607/88 |
| 6,053,936 | A * | 4/2000 | Koyama et al. | 607/88 |
| 6,459,919 | B1 * | 10/2002 | Lys et al. | 600/407 |
| 6,706,071 | B1 | 3/2004 | Wolter | |
| 6,875,225 | B1 | 4/2005 | Pederson et al. | |
| 2003/0206411 | A9 * | 11/2003 | Dowling et al. | 362/234 |
| 2003/0233138 | A1 * | 12/2003 | Spooner | 607/93 |
| 2005/0015122 | A1 * | 1/2005 | Mott et al. | 607/88 |
| 2005/0063194 | A1 * | 3/2005 | Lys et al. | 362/545 |
| 2006/0009822 | A1 * | 1/2006 | Savage et al. | 607/88 |
| 2008/0091250 | A1 * | 4/2008 | Powell | 607/90 |

OTHER PUBLICATIONS

Kessler et al.. The epidemiology of major depressive disorder: results from National Comorbidity Survey Replication (NCS-R). JAMA 2003.18; 289(23): 3095-105.

Rosen LN, et al Psychiatry Research, 1990, 31: 131-144.

Kasper S. et al Archives of General Psychiatry, 1989, 46: 823-833.

Thompson C et al. : J Affect Disord. Mar. 2004; 78(3):219-26.

Wirz-Justice A, Graw P, Krauchi K, Wacker HR. Seasonality in affective disorders in Switzerland. Acta Psychiatr Scand Suppl. 2003;(418):92-5.

Elbi H, Noyan A et al., Seasonal affective disorder in eight groups in Turkey: a cross-national perspective. J Affect Disord. Jun. 2002;70(I):77-84.

Gotestam KG, Skarderud F, Rosenvinge JH, Vedul-Kjelsas E. Pathological overeating—an overview Tidsskr Nor Laegeforen. Aug. 26, 2004;124(16):2118-20.

Corman B, Leger D. Sleep disorders in elderly. Rev Prat. Jun. 30, 2004; 54(12):1281-5.

Tuunainen A, Kripke DF, Endo T. Light therapy for non-seasonal depression. Cochrane Database Syst Rev. 2004;(2): CD004050.

Rosenthal et al. Seasonal affective disorder. A description of the syndrome and preliminary findings with light therapy. Arch Gen Psychiatry. Jan. 1984; 41(I):72-80.

Magnusson A, Boivin D. Seasonal affective disorder: an overview. Chronobiol Int. Mar. 2003;20(2): 189-207.

Levitt AJ, Lam RW, Levitan R. A comparison of open treatment of seasonal major, and minor depression with light therapy. J Affect Disord. Sep. 2002;71(I-3):243-8.

Kripke DF. Light treatment for non-seasonal depression: speed, efficacy, and combined treatment. J Affect Disord. May 1998;49(2):109-17.

Thalen BE, Kjellman BF, Morkrid L, Wibom R, Wetterberg L. Light treatment in seasonal and nonseasonal depression Acta Psychiatr Scand. May 1995; 91(5):352-60.

Levitan RD, Kaplan AS, Rockert W. Characterization of the "seasonal" bulimic patient. Int J Eat Disord. Mar. 1996; 19(2): 187-92.

Braun DL et al., Bright light therapy decreases . . . nervosa: a double-blind, placebo-controlled study. Compr Psychiatry. Nov.-Dec. 1999;40(6):442-8circ.

Lam RW et al., An open trial of light therapy for women with seasonal affective disorder and comorbid bulimia nervosa. : J Clin Psychiatry. Mar. 2001;62(3): 164-8.

Cole PJ, Smith JS, Alcala YC, Elliott JA, Kripke DF. Bright-light mask treatment of delayed sleep phase syndrome. J Biol Rhythms. Feb. 2002;17(I):89-101.

Sutherland D5 Woodward Y, Byrne J, Allen H, Bums A. The use of light therapy to lower agitation in people with dementia. Nurs Times. Nov. 9-15, 2004; 100(45):32-4.

Fontana Gasio P, et al., Dawn-dusk simulation light therapy of disturbed circadian rest-activity cycles in demented elderly. Exp Gerontol. Jan.-Feb. 2003; 38(I-2):207-16.

Skjerve A. et al. Improvement in behavioral symptoms . . . dementia. Psychiatry Clin Neurosci. 2004; 58(4): 343-7.

Skjerve A. et al. Light Therapy for behavioural and psychological symptoms of dementia.Int J Geriatr Psychiatry. 2004; 19(6): 516-22.

Pjrek E et al., Menstrual disturbances a rare side-effect of bright-light therapy. Int J Neuropsychopharmacol. Jun. 2004;7(2):239-40. Epub Feb. 13, 2003.

Terman M, Tennan JS Bright light therapy: side effects and benefits across the symptom spectrum. : J Clin Psychiatry. Nov. 1999;60(II):799-808; quiz 809.

Epperson CN et al., Randomized clinical trial of bright light therapy for antepartum depression: preliminary findings. J Clin Psychiatry. Mar. 2004; 65(3):421-5.

Gallin PF et al., Ophthalmologic examination of patients with seasonal affective disorder, before and after bright light therapy. Am J Ophthalmol. Feb. 1995;119(2):202-10.

Oren DA et al., An open trial of morning light therapy for treatment of antepartum depression. Am J Psychiatry. Apr. 2002; 159(4):666-9. Am J Psychiatry. 2002.

Dennis CL, Stewart DE. Treatment of postpartum depression, part 1 : a critical review of biological interventions. J Clin Psychiatry. Sep. 2004; 65(9): 1242-51.

Praschak-Rieder N et al., Prevalence of premenstrual dysphoric disorder in female patients with seasonal affective disorder. J Affect Disord. Mar. 2001;63(I-3):239-42.

Lam RW et al., A controlled study of light therapy in women with late luteal phase dysphoric disorder. Psychiatry Res. Jun. 30, 1999; 86(3): 185-92.

Kennedy SH et al., CANMAT Depression Work Group, Clinical guidelines for . . . biological treatments. Can J Psychiatry. Jun. 2001; 46 Suppl I:38S-58S.

Tam EM, Lam RW, Levitt AJ. Treatment of seasonal affective disorder: a review Can J Psychiatry. Oct. 1995; 40(8): 457-66.

Meesters Y et al., Prophylactic treatment of . . . infrared light? Biol Psychiatry. Jul. 15, 1999;46(2):239-46.

Blehar MC et al., Seasonal affective disorders and phototherapy. Report of . . . workshop. Arch Gen Psychiatry. May 1989;46(5):469-74.

Avery DH, et al. Affect Disord. May 2002;69(I-3):231-6.

Avery DH et al, Dawn simulation and bright light in the treatment of SAD: a controlled study. Biol Psychiatry. Aug. 1, 2001; 50(3):205-16.

Giedke H, et al. Sleep Med Rev. Oct. 2002;6(5):361-77.

Praschak-Rieder N, Willeit M, Neumeister A, Hilger E, Kasper S. Therapeutic sleep deprivation and phototherapy Wien Med Wochenschr. 1999;149(18):520-4.

Loving RT, et al. Depress Anxiety. 2002; 16(1): 1-3.

Neumeister A, et al., Biol Psychiatry. Jan. 1, 1996; 39(1): 16-21.

Cocilovo A. Colored light therapy: overview . . . combined with acupuncture. Am J Acupunct. 1999; 27(I-2):71-83.

Wright HR et al., Differential effects of light wavelength in phase advancing the melatonin rhythm. J Pineal Res. Mar. 2004; 36(2): 140-4.

Cajochen C et al., High sensitivity of human melatonin, alertness, thermoregulation and heart rate to short wavelength light. Clin Endocrinolog Metab. 2005; 90(3): 1311-6.

Glickman G. et al. Light Therapy for Seasonal Affective Disorder with Blue Narrow-Band Light-Emitting Diodes'(LED's). Biol Psychiatry Sep. 13, 2005.

Wright HR, Lack LC,Partridge KJ. Light emitting diodes can be used to phase delay the melatonin rhythm. J Pineal Res. Nov. 2001;31(4):350-5.

Benedetti F et al., Morning light treatment hastens . . . A placebo-controlled trial. J Clin Psychiatry. Jun. 2003;64(6):648-53.

van den Bossche RA et al., The teenager . . . underlying sleep disorder. Ned Tijdschr Geneeskd. Feb. 14, 2004;148(7):301.

European patent application No. EP1850912 (parallel case in Europe) through Oct. 6, 2011, EPO.

Office Action for counterpart Israel application No. IL 185243, Document Date: Feb. 14, 2010, Site Upload Date: Aug. 28, 2012.

Applicant response to notice of objections for counterpart Israel application No. IL 185243, Document Date: May 22, 2012, Site Upload Date: Aug. 28, 2012.

Office Action for counterpart Israel application No. IL 185243, Document Date: Aug. 11, 2013, Site Upload Date: Aug. 13, 2013.

International Preliminary Report on Patentability of the corresponding PCT application—4 pages, Oct. 3, 2007.

* cited by examiner

APPARATUS AND METHOD FOR PROVIDING A MULTI-STAGE LIGHT TREATMENT

CLAIM OF PRIORITY

This application claims priority to PCT/IL2006/000212 filed on Feb. 19, 2006, which claims priority to U.S. provisional patent application Ser. No. 60/653,998, filed on Feb. 18, 2005.

FIELD OF THE INVENTION

The present invention relates to light treatment useful for treating psychiatric, mood and/or circadian rhythm disorders, and to apparatus for providing the same.

BACKGROUND

According to WHO data, psychiatric disorders are considered to be the second between the seven leading global health problems in the world today (1). Depression is a common disorder, widely distributed in the population with 16.2% prevalence and is associated with substantial symptom severity and role impairment (2). Seasonal Affective Disorder (SAD) is also common in certain areas of the world, with prevalence rates increasing with latitude: about 10% in Alaska and Canada (3,4), between 5.6-10.7% in UK (5), 8.9% in Central Europe (6) and only 3.7-6.6% in Turkey (7). Another major medical problem of the western civilization is Binge Eating Disorder. 6% of women population of the world will suffer from this eating disorder sometime during their life. (8). Sleep disorders as insomnia and sleep schedule disorders affect as much as 20% of the adult population and is increasing with age (9). Light Therapy is an evidence based medical noninvasive therapy that has been recently evaluated by a larged review study (10) and considered as an "effective non-drug treatment" for depression and many other troublesome medical problems as listed above. The State of the art of the Broad Spectrum Bright Light Therapy (BLT) is well established in the scientific literature (235 published studies) from 1984 (11) until today. It is used to treat seasonal (12, 13) and nonseasonal depression (14, 15), binge eating (16,17,18) and sleep and circadian rhythm disorders (19,20), including sleep problems of the demented patient (21, 22, 23, 24). Because of its minimal side effects profile (25, 26, 27), BLT has been successfully used in antepartum depression (28, 29), postpartum depression (30) and premenstrual dysphoric disorder (31, 32). The Canadian Psychiatric Association Clinical Guidelines (33) considers light therapy as a first line treatment in seasonal affective disorder. BLT implies the use of a Light Box (34) that uses fluorescent or neon light sources capable of producing wide/broad-spectrum white light between 2500-10000 lux. The Light Boxes usually filter the UV light (below 400 nm). The therapy consists of early morning exposure for about 30-60 minutes every day. An alternative to Light Box is the Light Visor, a small light device mounted on the head that produces 2000 lux bright light directly to the eyes (35). U.S. Pat. No. 6,875,225 discloses a light therapy device capable of generating 2,500 lux to 7,500 lux at 12 inches.

The biologic mechanism of light therapy involves the activation via optic pathways of the suprachiasmatic nucleus of the hypothalamus, inhibition of the melatonin production by the pineal gland and increase of the central serotonin level in the limbic system. (36). Another well-studied light therapy is Dawn/Dusk Simulation (DS)(37, 38). This therapy is acting on the melatonin cycle and is based on gradual increases of light while the patient is asleep, until a maximum brightness of 400 lux is achieved, thus mimicking the natural sunrise or sunset. According to some consistent studies (38), DS is as effective as BLT, but have a better compliance because it works while the patient is steel asleep. The existing dawn simulators are using bulbs capable of gradually (30-60 minutes) increasing the light to a maximum 400 lux only. Another well recognized non-pharmacologic therapy for depression is Sleep Deprivation (Wake Therapy). About 40-60% of the depressive symptoms improve after one night of sleep deprivation or after partial sleep deprivation of the second part of the night (39). Combined sleep deprivation and light therapy have been described in the literature (40,41,42), and considered to be superior to each therapy alone. Color Light Therapy is actually used as a traditional oriental medicine (acupuncture, ayurveda) (43).

All existing light devices have many limitations: The compliance of the patients using Light Boxes may be problematic because the treatment must be followed every day at early morning hours, while the patient is fully awake and the distance and the position of the device must be controlled. All these parameters are important for the efficacy of the treatment, but they depend on the cooperation with the patient and his understanding of the method. Light Visors are considered less effective than Light Boxes, the light brightness is of only 2000 lux but very close to the eyes, thus provoking unpleasant eye irritation. The dawn simulators are based on a different light therapy method (simulating the natural dawn) and have a better compliance because it works while the patient is asleep, but the spectrum and brightness are limited (e.g. maximum 400 lux), which are not enough for a true BLT. Wake therapy is not a device but a method and is not actually used in the clinical practice because when used alone, its antidepressant effect is transient. Recently, some devices using specific colors of the spectrum (green, blue) has been considered as equivalent to BLT, but the research in this direction is still limited. For example, WO 2005/004948 discloses a method for modifying or resetting the circadian cycle using short wavelength light.

Novel, effective, evidence based non-drug treatments for depression, anxiety, eating and sleep disorder are important challenges of the third millennium for a number of reasons: (1) minimal side effects compared to medication (2) better compliance with non-drug treatments (3) no stigmatization (3) minimal risk for pregnant women (4) not affecting lactation in postpartum depressed women (4) minimal interaction with other medication in poli-medicated patients. For all these reasons, a new Light Therapy method that overcomes the limitations of the existing light therapy methods and devices is needed.

SUMMARY OF THE INVENTION

One or more of the aforementioned needs are satisfied by several aspects of the present invention.

It is now disclosed for the first time apparatus comprising: (a) a light source; and (b) a controller said controller operative to (i) effect, using said light source, a first stage of light emission including a first time window of 20 minutes during which, for a majority of the time of said first time window, the light intensity at a predetermined distance is equal to at least a low-intensity minimum value of at least about 50 lux and is equal to at most a low-intensity maximum value of at most about 2000 lux (ii) to effect, subsequent to said first time window, using said light source, a second stage of light emission including a second time window of at least 60 minutes wherein for every 45 minute sub-window within said second time window, the light intensity at said predetermined distance, for a majority of the time of said sub-window, is equal to at least a second minimum value of at least about 100 lux; and (iii) to effect, subsequent to said second time window, using said light source, a third stage of light emission including a third time window of at least 20 minutes during which, for a majority of the time of said third time window, the light intensity at said predetermined distance is equal to at least a high-intensity minimum value of at least about 2000 lux, wherein said predetermined distance is a distance selected from the group consisting of 20 cm, 30 cm, 45 cm, 55 cm, 70 cm, and 100 cm.

According to some embodiments, wherein the controller is configured such that for every 30 minute sub-window within said second time window, It is noted that the term "sub-window within the second time window" refers to a time window that is contained within the "second time window."

According to some embodiments, the low-intensity minimum value is 100 lux, or 200 lux, or 300 lux, or 400 lux.

According to some embodiments, the low-intensity maximum value is 2000 lux, or 1500 lux, or 1200 lux, 1000 lux, or 800 lux.

According to some embodiments, the apparatus is configured such that an intensity emitted from said light source at said predetermined distance during a majority of the time of said second time window and during a majority of the time of said third time windows is at most 20,000 lux.

According to some embodiments, the apparatus is configured such that an intensity emitted from said light source at said predetermined distance during a majority of the time of said second time window and during a majority of the time of said third time windows is at most 15,000 lux.

According to some embodiments, the apparatus is configured such that an intensity emitted from said light source at said predetermined distance during a majority of the time of said second time window and during a majority of the time of said third time windows is at most 12,000 lux.

According to some embodiments, said controller is operative to effect said first, second and third stages such that an elapsed time between a beginning of said first time window and a beginning of said third time window is at most a maximum elapsed time value of 8 hours.

According to some embodiments, said controller is operative to effect said first, second and third stages such that an elapsed time between a beginning of said first time window and a beginning of said third time window is at most a maximum elapsed time value of 6 hours.

According to some embodiments, said light source includes a plurality of LEDs.

According to some embodiments, at least some said LEDS are white LEDS and at least some said LEDs are colored LEDS.

According to some embodiments, said low-intensity minimum value is at least 600 lux.

According to some embodiments, said controller is configured such that said first stage of light treatment includes a simulated dawn process wherein the intensity of light gradually at said predetermined distance increases from substantially zero lux (for example, less than 50 lux) to between 500 lux and 1200 lux over a period of between 30 minutes and 75 minutes.

According to some embodiments, said controller is configured such that said first time window is preceded by an lower intensity time window of 20 minutes during which, for a majority of the time, the light intensity at said predetermined distance is equal to at least a lower-intensity minimum value of 100 lux and is equal to at most a lower-intensity maximum value of 400 lux.

According to some embodiments, said controller is configured such that said second window includes a fourth time window of at least 45 minutes wherein for every 10 minute period within said fourth time window, the light intensity at said predetermined distance is equal to at most a value of 1500 lux.

According to some embodiments, said controller is configured such that for every said 10 minute period within said fourth time window, the light intensity at said predetermined distance is equal to at least a value of 2500 lux.

According to some embodiments, said controller is configured such that for every non-overlapping 15 minute period within said second time window, a value of an average light intensity at said predetermined distance during a latter said non-overlapping time period exceeds or is substantially equal to a value of an average light intensity at said predetermined distance during an earlier said non-overlapping time period.

According to some embodiments, said controller is configured such that a duration of said second time window is at least 150 minutes.

According to some embodiments, said controller is configured such that a duration of said second time window is at least 180 minutes.

According to some embodiments, said high-intensity minimum value is 5000 lux, or 7500 lux, 9500 lux.

According to some embodiments, said controller is configured such that said third stage further includes a fourth time window of 60 minutes distinct from said third time window, during which, for a majority of the time, the light intensity at said predetermined distance is equal to at least said high-intensity minimum value.

According to some embodiments, said controller is configured such that at least one of light emitted from said light source of said majority of the time of said first window and light emitted from said light source of a majority of the time of said second window comprises both white light and colored light having a wavelength of less than 550 nanometers.

According to some embodiments, said controller is configured such that said light emitted from said light source of said majority of the time of said first window comprises at least 5% colored light and at most 30% colored light.

According to some embodiments, said controller is configured such that said light emitted from said light source of said majority of the time of said second window comprises at least 20% colored light and at most 60% colored light.

According to some embodiments, said colored light having a wavelength of less than 550 nanometers is green light having a wavelength between 520 nm and 535 nanometers.

According to some embodiments, said controller is configured such that at least one of light emitted from said light source of said majority of the time of said first window and light emitted from said light source of a majority of the time of said second window comprises at least 40% white light According to some embodiments, said controller is configured to effect said first, second and third stages for a plurality of days at a time that is substantially the same time of day.

According to some embodiments, said controller is configured to effect said first, second and third stages for at least one day, and on days following said at least one day, said controller is configured to effect at least one day to a fourth stage of light treatment, wherein: (i) said fourth stage of light treatment includes at least 30 minutes of high intensity light treatment administered within a 60 minute period and administered at a time of day substantially identical to a time of day of said third time window, and (ii) a duration of said fourth stage is equal to at most 30% less than an elapsed time between a beginning of said first time window and an end of said second time window.

According to some embodiments, the apparatus is configured such that light emitted from said light source said during majority of the time of said first time window of said first stage comprises at least 50% white light (i.e. broad spectrum white light).

According to some embodiments, the apparatus is configured such that light emitted from said light source said during every said majority of the time of said second time window of said second stage comprises at least 50% white light (i.e. broad spectrum white light).

According to some embodiments, the apparatus is configured such that light emitted from said light source said during majority of the time of said third time window of said third stage comprises at least 50% white light (i.e. broad spectrum white light).

According to some embodiments, said second minimum value is 300 lux, or 400 lux, or 500 lux, or 750 lux, or 1000 lux, or 1250 lux, or 1500 lux.

According to some embodiments, said controller is configured such for every 30 minute sub-window within said second time window the light intensity at said predetermined distance, for a majority of the time, is equal to at least said second minimum value According to some embodiments, said controller is configured such for every 20 minute sub-window within said second time window the light intensity at said predetermined distance, for a majority of the time, is equal to at least said second minimum value.

According to some embodiments, said controller is configured such for every 10 minute sub-window within said second time window the light intensity at said predetermined distance, for a majority of the time, is equal to at least said second minimum value.

According to some embodiments, said controller is configured such that a duration of said second time window is at least 120 minutes.

According to some embodiments, said controller is configured such that a duration of said second time window is at least 90 minutes.

According to some embodiments, said controller is configured such that a duration of said third time window is 40 minutes.

According to some embodiments, said controller is configured such that a duration of said third time window is 60 minutes.

According to some embodiments, said controller is configured such that a duration of said third time window is 75 minutes.

According to some embodiments, the apparatus is adapted to shut off (i.e. shut off at least the light source, and optionally the electronics of the controller) no later than 120 minutes after the end of said third window.

According to some embodiments, the apparatus is adapted to shut off no later than 60 minutes after the end of said third window.

According to some embodiments, the apparatus is adapted to shut off no later than 30 minutes after the end of said third window.

According to some embodiments, the apparatus is adapted to shut off no later than immediately after the end of said third window.

Alternatively, instead of completely shutting off the apparatus (or at least the light source of the apparatus), the controller of the device may be adapted to lower the intensity of the light after the bright light therapy provided by the device has concluded.

According to some embodiments, controller is further operative to (iv) effect, no later than immediately after 60 minutes after the end of said third time window (or alternatively, no later than immediately after the end of said third time window), a decreased light stage whose duration is at least 20 minutes, wherein an intensity of light emitted from said light source at said predetermined distance is at most a fraction whose value is at most 0.99 of said high-intensity minimum value According to some embodiments, a duration of said decreased light stage is at least 60 minutes, or alternatively, at least 120 minutes.

According to some embodiments, said value of said fraction is about 0.9, or alternatively about 0.7, about 0.5, about 0.3, about 0.2, about 0.1, about 0.1, or about 0.01.

According to some embodiments, the apparatus and/or controller is configured such that for a majority of the time of said second time window, the light intensity at said predetermined distance is equal to at most a second maximum value of at most about 10,000 lux. In different embodiments, the value of the second maximum value may be 10,000 lux, 7,500 lux, 5,000 lux, 2,500 lux, 2,000 lux and 1,500 lux.

It is noted that the presently disclosed apparatus is useful for treating at least one of a psychiatric disorder, a mood disorder and a circadian rhythm disorder.

These and further embodiments will be apparent from the detailed description and examples that follow.

DETAILED DESCRIPTION OF THE INVENTION

The present invention will now be described in terms of specific, example embodiments. It is to be understood that the invention is not limited to the example embodiments disclosed. It should also be understood that not every feature of the apparatus and method for providing light treatment described is necessary to implement the invention as claimed in any particular one of the appended claims. Various elements and features of devices are described to fully enable the invention. It should also be understood that throughout this disclosure, where a process or method is shown or described, the steps of the method may be performed in any order or simultaneously, unless it is clear from the context that one step depends on another being performed first.

The present inventor is now disclosing an apparatus and a method for providing a novel light treatment for a number of psychiatric, mood and circadian rhythm disorders, including, but not limited to non-seasonal depression, premenstrual syndrome, binge eating, seasonal depression and circadian rhythm disorders.

According to some embodiments, the presently disclosed treatment provides sleep deprivation by light (i.e. extended sleep deprivation of at least 2½ hours, more preferably at least 3 hours, most preferably at least 3½ hours) in combination with bright light therapy. Typically, the patient is awakened with a simulated dawn process, and then subjected, for an extended period of time, to light that is bright enough to keep the patient awake and includes a phase of "bright light" therapy. Optionally, the patient is subjected to a mixture of white light (i.e. broad spectrum white light) and medium wavelength light.

Thus, it is noted that the presently disclosed light treatment may provide up to four synergistic therapies: sleep deprivation therapy (for example, extended sleep deprivation therapy), bright light therapy, dawn simulation therapy, and medium wavelength light therapy.

The Multi-Stage Therapy

Figure 1A:
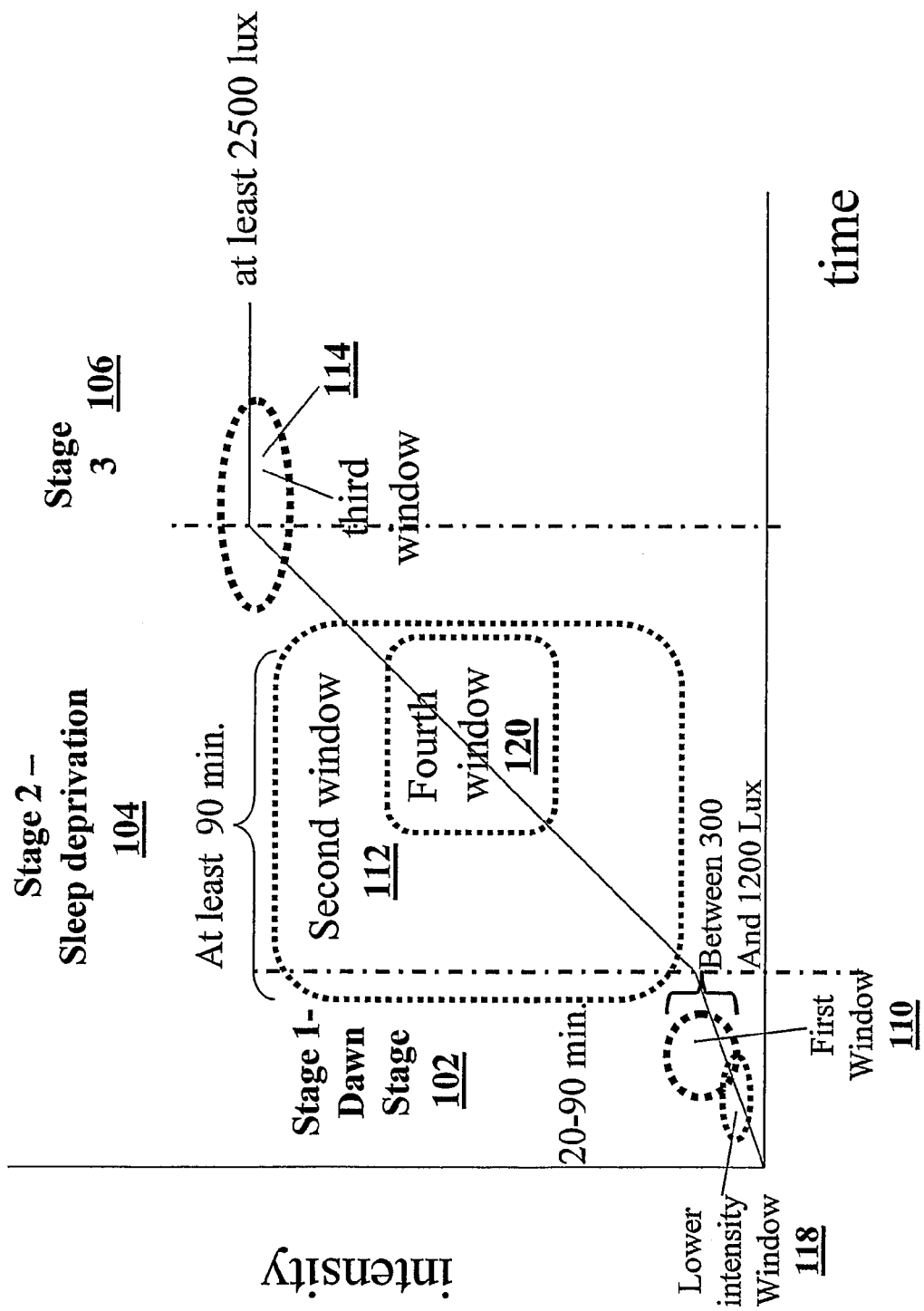
FIG. 1A-1B illustrate a graph of light intensity as a function of time according to exemplary embodiments of the present invention.
Figure 1B:
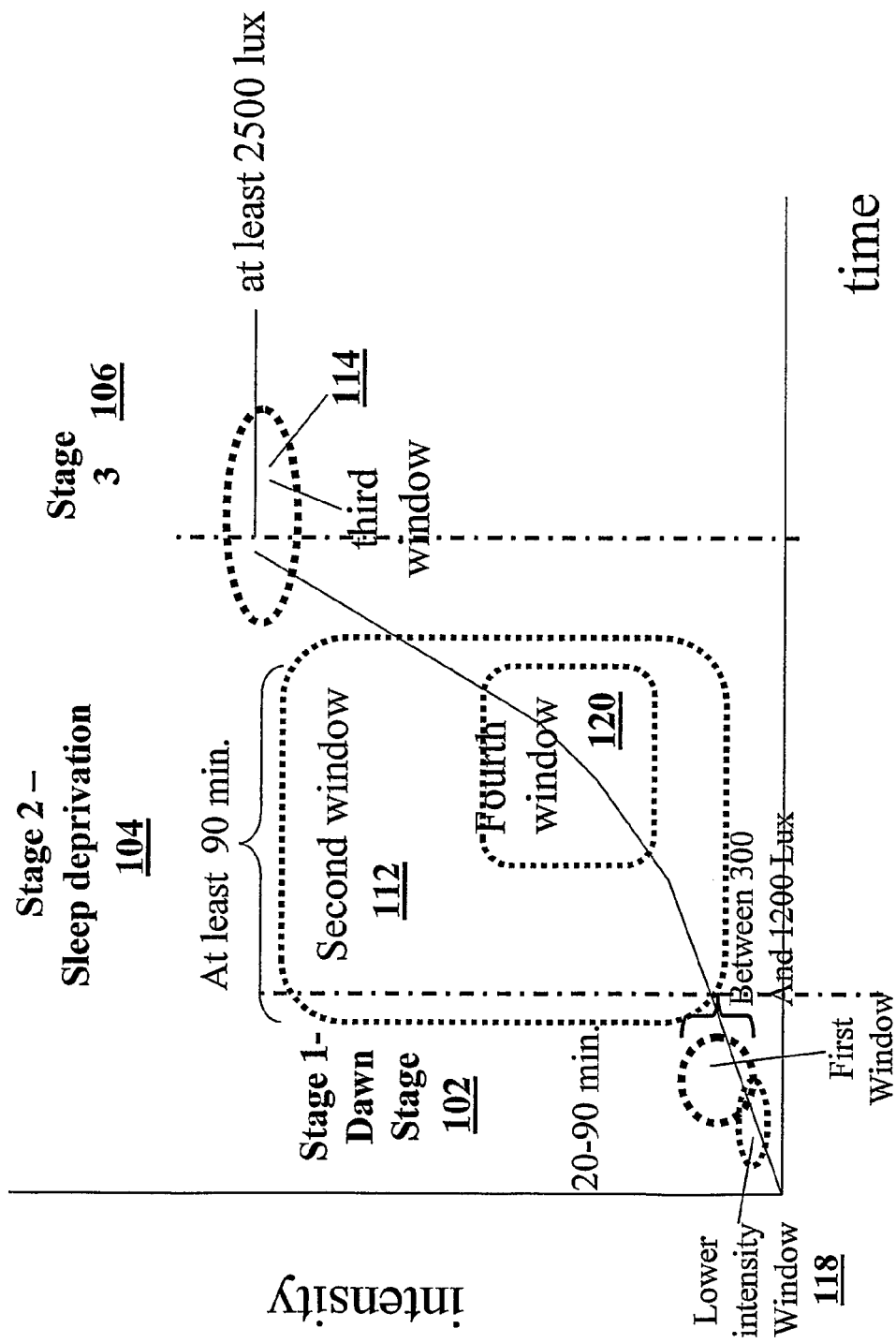

According to some embodiments, a novel light treatment comprising several stages is administered to a patient. This multi-stage light treatment protocol will be explained with reference to FIGS. 1A-1B, which provides exemplary graphs of the light intensity (for example, at a distance of about 18 inches from the light source, for example, near the patient's eyes) as a function of time. It is noted that the graphs of FIGS. 1A-1B are not to scale.

Stage 1

Dawn Simulation 102

During the first stage 102, the patient is subjected to a light treatment which includes a first time window 110 of 20-40 minutes (for example, 20 minutes) during which, for a majority of the time, the light intensity is equal to at least a low-intensity minimum value of 50 lux and is equal to at most a low-intensity maximum value of 2000 lux. Preferably, the low-intensity minimum value is 300 lux and the low-intensity maximum value is 1200 lux, though this should not be construed as a limitation.

Not wishing to be bound by theory, it is noted that typically, the purpose of the first stage of light treatment is to wake the patient gently, so as not to agitate the patient, but firmly, in order that the patient remain awake and not return to sleep. Thus, it is noted that a light intensity of less than 300 lux would probably not suffice to wake many patients, though this exact number could, of course, vary between patients. Furthermore, it is noted that this first time window is typically often provided in the context of a "dawn stage" 102 to awaken a slumbering patient. Thus, it is noted that if, during the course of this simulated dawn process, the light intensity exceeds 1200 lux, many patients could get agitated (though this too could vary among patients), which may be an undesirable outcome.

Typically, this simulated dawn process is characterized by a gradual increase in light intensity, from an extremely low intensity of light (i.e. less than 200 lux, or preferably less than 100 lux) to an intensity whose value is equal to at least the low-intensity minimum value and at most the low-intensity maximum value. As used herein, a "gradual increase" refers to a gradual increase as experienced by the user and includes cases where there are transient variations that do not significantly impact on the overall effect experienced by the patient. In different embodiments, the simulated dawn process 102 has of duration between 20 and 90 minutes including the first window 110. Preferably, the simulated dawn process has a duration of between 30 minutes and 75 minutes.

It is appreciated that because different individuals have different sensitivities to light (i.e. require a different amount of ambient light in order to remain awake, and are able to tolerate a different amount of ambient light without feeling agitated) the exact intensity for any given individual during the time of the first window 110 may vary as a function of the patient subjected to the light treatment. For example, for certain individuals, who are "heavier sleepers," the low-intensity minimum value may be set to be at least 600 lux, or at least 800 lux.

Similarly, some individuals are more likely to be agitated by light of a greater intensity upon waking up than others. Thus, for these more sensitive patients, the low-intensity maximum value may be set to be less than 1200 lux, for example, at most 1000 lux, or lower.

As noted earlier, the first window 110 is typically provided within the context of a dawn simulation characterized by a gradual increase in the light intensity. Thus, it is noted that in exemplary embodiments, the first time window 110 is proceeded by another "lower intensity time window 118" where the light intensity is even lower, for example, between a lower-intensity minimum value of 100 lux and a lower-intensity maximum value of 400 lux. During this time lower intensity time window, the light intensity typically gradually increases gradually.

In some embodiments, the device providing the light treatment is configured such that the first window 110 is begins after only 1-4 hours of sleep, so as to wake the patient in the middle of a night's sleep and to deprive the patient of sleep.

Stage 2

Extended Sleep Deprivation 104

After the dawn stage 102, the patient is subjected to a second stage 104 of light treatment, where the intensity of light is maintained at a level so as to deprive the patient of sleep. This second stage 104 of light treatment includes a second time window 112 of at least 90 minutes wherein for every 10 minute period, the light intensity, for a majority of time, is equal to at least a second minimum value of 100 lux. This intensity should be sufficient to keep the patient awake. Thus, it is appreciated that for some patients, a second minimum value of 300 lux, or 500 lux, or of 1000 lux, or of 1500 lux is desired to keep the patient awake.

Nevertheless, it will be appreciated that the exact intensity required to keep any specific patient awake may vary between patients. Thus, in some embodiments, the second minimum value is at least 1000 lux, or alternatively at least 1500 lux, or alternatively at least 2000 lux.

Although periods of time where the intensity of light decreases are not outside of the scope of the invention, it is noted that typically the light intensity is constant or increasing as a function of time, throughout the majority of time of the second stage 104, and in particular during part, the majority, or substantially the entire the second time window 112, in order to avoid an impression of a setting sun which may hinder the sleep deprivation process. In general, the exact profile of light intensity as a function of time required to maintain the wakeful state of any given patient will also vary between patients.

Although the minimum duration of the second time window is usually 90 minutes, it is appreciated that certain patients may require a longer period of sleep deprivation than others. Thus, in some embodiments, the second time window is at least 150 minutes, and in some embodiments, the second time window is at least 180 minutes.

Not wishing to be bound by theory, it is further noted that the second stage 104 of light treatment, and in particular the second window 112, may provide a transition between the period of low intensity light treatment (i.e. that of the first window 110), and the period of high intensity light treatment (i.e. that of the third window 114).

Thus, it is appreciated that while not an explicit limitation of the present invention, sudden changes in the light intensity are preferably to be avoided during the second window 112 in order to avoid unnecessarily agitating the patient. As such, in some embodiments, the second window 112 includes a period of time when the intensity of light gradually increases.

The rate of increase need not be substantially constant, as in the example of FIG. 1A. In some embodiments (for example, as illustrated in FIG. 1B) the rate of increase towards the end of the period of time of the second window 112 is greater than the rate of increase in the beginning of the second window 112. This "crescendo effect" may allow for a smooth increase in light intensity without overexposing the patient to too long a period of time of intense light. This intensity profile may be useful for embodiments where the light intensity during the third window 114 is on the order of magnitude of 6,000-10,000 lux.

Thus according to some embodiments such as embodiments providing this "crescendo effect", for at least at least a plurality of non-overlapping 15 minute period within the second time window, or for every non-overlapping 15 minute period within the second time window, a value of the average light intensity during a latter non-overlapping time period exceeds or is equal to a value of the average light intensity during an earlier non-overlapping time period.

It is noted that the present inventor is disclosing a synergy between extended sleep deprivation and bright light therapy. Optionally, the light therapy may be augmented with music in order to help the patient remain awake during the period of treatment.

Stage 3

Bright Light Therapy 106

The benefits of bright light therapy for certain mood and psychiatric disorders are well known. The present inventor is disclosing that the subjecting the patient to a protocol which provides extended sleep deprivation as well as bright light therapy provides a synergistic effect which is useful for treating these disorders.

During the third stage, bright light therapy is thus provided. In particular, the third stage includes a third time window of 30-60 minutes (for example 60 minutes) during which light intensity is equal to at least a high-intensity minimum value.

It is noted that in the literature, there are different opinions upon the minimum intensity required to provide bright light therapy for treating mood and psychiatric disorders, with some investigators reporting a bright light therapy at an intensity of 10,000 lux, while other investigators have reported a bright light therapy at an intensity of 5,000 lux, while other investigators have reported a bright light therapy at an intensity of 2,500 lux.

Thus, it is noted that in some embodiments, the high intensity minimum value of the third window 114 is 9,500 lux.

In some embodiments, the high intensity minimum value of the third window 114 is 5,000 lux.

In some embodiments, the high intensity minimum value of the third window 114 is 2,500 lux.

Furthermore, as illustrated in FIGS. 1A-1B, the light intensity during this third window 114 remains substantially constant, though this is certainly not a limitation, and embodiments where the light intensity fluctuates while remaining above the "high intensity minimum value" during the majority of the 60 minute period of the third window 114 are contemplated.

It is noted that in many situations, exposure to light that is too bright may be discomforting or damaging to the patient, and thus, in some embodiments, the light intensity is kept below certain values (for example 20,000 lux, or below 15,000 lux, or below 10,000 lux) during periods of time in the second and third time windows.

Furthermore, it is noted that in some embodiments, the amount of time of bright light therapy may be extended beyond what is illustrated in FIGS. 1A-1B.

Duration of the Treatment Protocol and Treatment on Subsequent Days

It is noted that typically, the three-stage light treatment protocol described herein is provided as a single treatment, and it is preferred that the patient remains in proximity of the light device throughout the period of time of treatment.

In exemplary embodiments, the total length of time of "single treatment" is typically between about 3 hours and usually no more than 6 hours. According to exemplary embodiments, the elapsed time between the beginning of the first time window 110 and the beginning of the third time window 114 is at most a maximum elapsed time value of 8 hours.

According to some examples, the total duration of light treatment is between 3½ and 5 hours including a 30 to 60 minutes "dawn simulation" stage, a second "sleep deprivation stage" of about 3 hours, and a third "bright light stage" of between 30 and 60 minutes.

White and Colored Light

It is noted that in the field of light therapy in general, and bright light therapy in particular, that broad spectrum white light is widely recognized as the "gold standard" for light treatment. Thus, in different embodiments, the light provided by the method and/or the apparatus is broad spectrum bright light. Nevertheless, it is noted that in different embodiments, this white light may be applied together with colored light, especially colored light having a wavelength of less than 550 nanometers, and preferably medium wavelength light therapy with light having a wavelength between 520 nm and 535 nm.

Thus, it is noted that optionally, medium wavelength light is provided, especially during the first 110 and second 112 time windows.

Not wishing to be bound by theory, it is noted that short to medium wavelength visible light (i.e. blue light of 460 nm, blue-green light of 497 nm, and green light of 525 nm) has been reported in the literature to be more effective for bringing the patient to a state of greater alertness (Wright et al, 2001, Cajochen 2005, Glickman 2005, Benedetti et all 2003).

In particular, recent research suggests that the circadian cycle receives photic input from photoreceptors not used for image-forming which are sensitive to specific wavelengths of light. More particularly, recent research reveals that the mammalian circadian pacemakers situated in the hypothalamic suprachiasmatic nuclei (SCN), receives environmental photic input (perceived environmental light and dark cycles) from a specialized set of ganglion cells.

The photic input entrains endogenous near 24-hour rhythms (including pineal rhythms) to the environmental 24-hour light-dark cycle, to maintain appropriate phase relationships between rhythmic physiological and behavioral processes and periodic environmental factors. In addition to entraining pineal rhythms, light exposure can acutely suppress melatonin secretion. Acute, light-induced melatonin suppression, a broadly used indicator for photic input to the SCN, has been used to elucidate the ocular and neural physiology for circadian regulation.

Furthermore, it is noted that medium wavelength light has been found to have a positive mood influencing effect (Benedetti 2003). Thus, providing medium wavelength light along with the broad spectrum white light may effective for providing yet another synergistic treatment of mood and psychiatric disorders in the context of sleep deprivation.

Thus, it is noted that in exemplary embodiments, the light of the first window 110 comprises between at least 5% and at most 30% short to medium wavelength visible light (preferably medium wavelength visible light having a wavelength between 520 and 535 nm). Not wishing to be bound by theory, it is noted that the combination of a gradual dawn process and medium wavelength light may be effective at gently but firmly waking the patient, leaving the patient in an alert state without overly agitating the patient.

Typically, during the second time window 112, the proportion of short to medium wavelength exceeds (for example, between 20% colored light and 60% short to medium wavelength light, preferably between 30% and 50% short to medium wavelength light) the proportion during the first window. As with the first time window 110, during the second time window 112 the short to medium wavelength light is preferably medium wavelength visible light having a wavelength between 520 and 535 nm Single or Multi-Day Treatment Protocol The presently disclosed therapy which provided extended sleep deprivation of at least 2½ hours, or at least 3½ hours, is administered for at least one day. In some embodiments, the therapy is administered two or more days, though typically not for more than five consecutive days. When the light therapy is administered for more than one day, it typically is administered at approximately the same time each day, though this should not be construed as limiting.

In some embodiments, the prolonged sleep deprivation light treatment is followed by one or more days of partial sleep deprivation (or advanced sleep deprivation) comprising a dawn simulation stage and a bright light therapy stage. This partial sleep deprivation stage typically provides light that exceeds 500 lux for up to 2½ hours, where the bright light treatment lasts at least 30 minutes.

In some embodiments, a treatment regimen including 1 to 5 days of extended sleep deprivation light therapy followed by partial sleep deprivation light therapy of 10 or more days (for example up to 30 days, for example more than 30 days) may be provided by a control unit operatively linked with a lighting fixture.

Novel Light Apparatus

Figure 2:
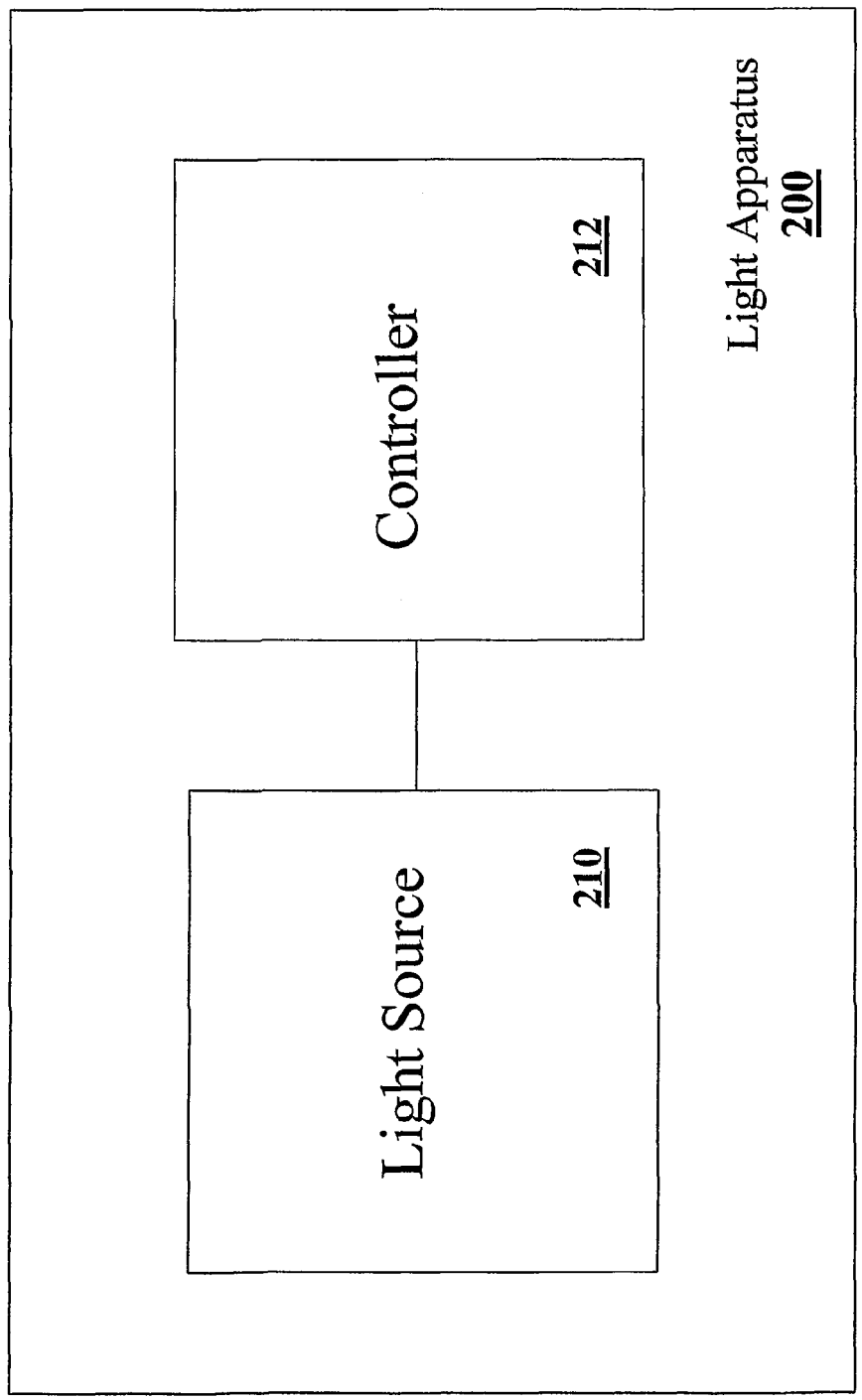
FIG. 2 provides a block diagram of a light treatment apparatus according to exemplary embodiments of the present invention.

The present inventor is disclosing for the first time a novel light apparatus for providing the aforementioned light treatments. A block diagram of this novel device is provided in FIG. 2. As is illustrated in FIG. 2, the light apparatus 200 includes a light source 210 and a controller 212.

Typically, the controller 212 includes an electronic circuitry (not shown) which can control the intensity of light as a function of time, and optionally the relative intensity of white and colored light as a function of time. Thus, the electronic circuitry includes a timer for controlling the duration for which light of any given intensity is emitted, and for controlling when a particular protocol beings. Optionally, the electronic circuitry of the controller 212 is operative to control is relative intensity of the white and colored lighting elements, and thus, may control the relative proportion of light of various colors. Typically, the controller 212 is operatively linked to a user interface (mechanical or electronic) where the user can conveniently select the program (i.e. using a single button, by entering in a number of another sequence of characters for specifying a given protocol, by selecting the protocol from a menu of protocols, etc) for providing the presently disclosed three stage light treatment, thereby obviating the need for the user to program in the desired treatment protocol himself.

Typically, the light provided by the light source 210 include broad spectrum white light, or is mostly broad spectrum white light.

In different embodiments, the presently disclosed controller 212 is operative to provide any light treatment method or protocol disclosed herein.

It is appreciated that the controller 212 may be provided as any appropriate combination of hardware and/or software elements.

There is no explicit limitation on the physical form of light source 210, as long as the light apparatus 200 as a whole is configured to provide, as a function of time, light having intensity specified by the parameters of the first, second and third time windows.

In general, light apparatus for providing light treatments are well known in the art, and in some embodiments, known light therapy devices may be modified (for example, operatively linked to controller 212) to provide the desired protocols. Thus, any light source 210 (for example, light apparatus including fluorescent lighting fixtures and light apparatus including a plurality of light emitting diodes (LEDs)) is within the scope of the present invention.

Figure 3:
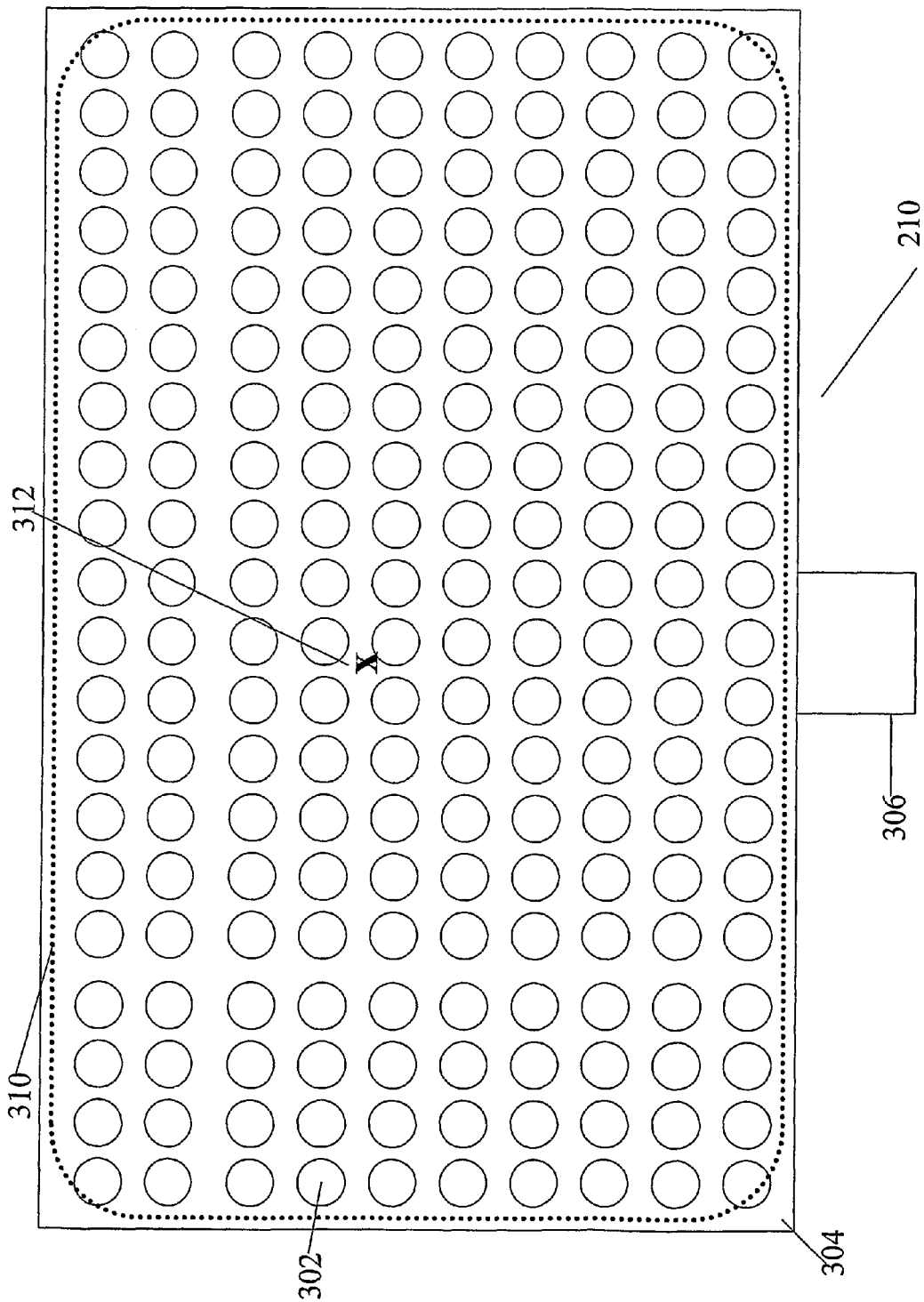
FIG. 3 provides an illustration of exemplary light source elements.

Preferably, as shown in FIG. 3, the light source 210 includes a light emitting assembly 310 in which a plurality of light emitting diodes (LEDs) 302 are mounted in an LED housing 304. It is noted that both "portable" devices within a portable housing 304, and "fixed" devices within a fixed housing 304 are both within the scope of the present invention.

According to the specific example of FIG. 3, the LED housing 304 is mounted on an "arm" 306 (drawn not to scale) and is supported by a base (not shown). In specific examples, the user interface (i.e. the control panel, not shown) may reside in or on the device base (not shown).

It is noted that the shape of the LED housing 304 shown in FIG. 3 is substantially rectangular, but this is not a limitation, and in some embodiments, LED housing 304 has a convex shape in order to focus the light on a specific region (for example, near the eyes of the patient). It is noted that in various embodiments, the light source 212 should include enough LEDs (or other lighting elements) to provide the requisite level of bright light therapy (for example, at least 2,500 at a given predetermined distance from the LED assembly 310, for example, at least 5,000 at the given predetermined distance from the LED assembly 310, for example, at least 10,000 at the given predetermined distance from the LED assembly 304).

It is noted that according to different embodiments, the patient may position the light source different distances from her face, and thus, the light treatment apparatus may provided may configured to provide the desired intensities of light at different values of the "predetermined distance." Preferably, the predetermined distance is 45 cm, though other values, such as 20 cm, 30 cm, 55 cm, 70 cm and 100 cm are all within the scope of the present invention.

Typically, devices which are configured to operate at a larger distance will include lighting elements (i.e. LEDs or fluorescent lighting elements) configured to emit light of a stronger intensity and/or more lighting elements, in order to provide light of a strong intensity such that the desired intensities are provided at a greater distance.

As used herein, a "light intensity at a predetermined distance" is the intensity measured at a the pre-determined distance (for example, a distance of 18 inches) from a 'central point' of the light source (for example, from a central point 312 of the LED assembly.

Optionally, the device includes a diffuser screen for providing a more uniform emission of light. Optionally, the diffuser screen includes an UV filter material.

It is appreciated that although the individual LEDS 302 in FIG. 3 are evenly spaced and substantially the same size, that this is not a limitation, and is merely illustrative.

Typically, the majority of the LEDS are "bright white LEDS" for emitting broad spectrum white light. Optionally, a certain number of LEDS are colored LEDs, for example, colored LEDs for emitting short to medium wavelength light, or green LEDs for emitting medium wavelength light. For embodiments that provide both white and colored LEDs, the controller 212 is operative to vary the proportion of white and colored light emitted by the device as a function of time.

REFERENCES

1 Word Health Report 1999: Seven leading global health problems estimated by DELY's lost.
2. Kessler et al., The epidemiology of major depressive disorder: results from National Comorbidity Survey Replication (NCS-R). JAMA 2003.18; 289(23): 3095-105
3. Rosen L N, et al. Psychiatry Research, 1990, 31: 131-144.
4. Kasper S. et al. Archives of General Psychiatry, 1989, 46: 823-833.
5. Thompson C et al.: J Affect Disord. 2004 March; 78(3): 219-26.
6. Wirz-Justice A, Graw P, Krauchi K, Wacker HR. Seasonality in affective disorders in Switzerland. Acta Psychiatr Scand Suppl. 2003; (418): 92-5
7. Elbi H, Noyan A, Korukoglu S, Unal S, Bekaroglu M, Oguzhanoglu N, Turkoz N, Abay E, Kumbasar H, Yurdakul S. Seasonal affective disorder in eight groups in Turkey: a cross-national perspective. J Affect Disord. 2002 June; 70(1): 77-84
8. Gotestam K G, Skarderud F, Rosenvinge T H, Vedul-Kjelsas E. Pathological overeating—an overview Tidsskr Nor Laegeforen. 2004 Aug. 26; 124(16): 2118-20
9. Corman B, Leger D. Sleep disorders in elderly. Rev Prat. 2004 Jun. 30; 54(12): 1281-5.
10. Tuunainen A, Kripke D F, Endo T. Light therapy for non-seasonal depression. Cochrane Database Syst Rev. 2004; (2): CD004050
11. Rosenthal N 1984 Rosenthal N E, Sack D A, Gillin J C, Lewy A J, Goodwin F K, Davenport Y, Mueller P S, Newsome D A, Wehr T A. Seasonal affective disorder. A description of the syndrome and preliminary findings with light therapy. Arch Gen Psychiatry. 1984 January; 41(1): 72-80.
12. Magnusson A, Boivin D. Seasonal affective disorder: an overview. Chronobiol Int. 2003 March; 20(2): 189-207
13. Levitt A J, Lam R W, Levitan R. A comparison of open treatment of seasonal major and minor depression with light therapy. J Affect Disord. 2002 September; 71(1-3): 243-8.
14. Kripke D F. Light treatment for nonseasonal depression: speed, efficacy, and combined treatment. J Affect Disord. 1998 May; 49(2): 109-17
15. Thalen B E, Kjellman B F, Morlkrid L, Wibom R, Wetterberg L. Light treatment in seasonal and nonseasonal depression Acta Psychiatr Scand. 1995 May; 91(5): 352-60
16. Levitan R D, Kaplan A S, Rockert W. Characterization of the "seasonal" bulimic patient. Int J Eat Disord. 1996 March; 19(2): 187-92.
17. Braun D L, Sunday S R, Formari V M, Halmi K A Bright light therapy decreases winter binge frequency in women with bulimia nervosa: a double-blind, placebo-controlled study. Compr Psychiatry. 1999 November-December; 40(6): 442-8 circ
18. Lam R W, Lee S K, Tam E M, Grewal A, Yatham L N. An open trial of light therapy for women with seasonal affective disorder and comorbid bulimia nervosa: J Clin Psychiatry. 2001 March; 62(3): 164-8.
19. van den Bossche R A, Peeters E A, de Weerd A W. The teenager who finds it difficult to wake up in the morning: aberrant behavior, misperception or an underlying sleep disorder? Ned Tijdschr Geneeskd. 2004 Feb. 14; 148(7): 301.
20. Cole R J, Smith J S, Alcala Y C, Elliott J A, Kripke D F. Bright-light mask treatment of delayed sleep phase syndrome. J Biol Rhythms. 2002 February; 17(1): 89-101
21. Sutherland D, Woodward Y, Byrne J, Allen H, Burns A. The use of light therapy to lower agitation in people with dementia. Nurs Times. 2004 Nov. 9-15; 100(45): 32-4.
22. Fontana Gasio P, Krauchi K, Cajochen C, Someren E, Amrhein 1, Pache M, Savaskan E, Wirz-Justice A. Dawn-dusk simulation light therapy of disturbed circadian rest-activity cycles in demented elderly. Exp Gerontol. 2003 January-February; 38(1-2): 207-16
23. Skjerve A. et al. Improvement in behavioral symptoms and advance of activity acrophase after short term bright light therapy in severe dementia.Psychiatry Clin Neurosci. 2004; 58(4): 343-7
24. Skjerve A. et al. Light Therapy for behavioural and psychological symptoms of dementia.Int J Geriatr Psychiatry. 2004; 19(6): 516-22
25. Pjrek E, Winkler D, Willeit M, Konstantinidis A, Thierry N, Kasper S. Menstrual disturbances a rare side-effect of bright-light therapy. Int J. Neuropsychopharmacol. 2004 June; 7(2): 239-40. Epub 2003 Feb. 13.
26. Terman M, Termian J S Bright light therapy: side effects and benefits across the symptom spectrum: J Clin Psychiatry. 1999 November; 60(11): 799-808; quiz 809
27. Epperson C N, Ternan M, Terman J S, Hanusa B H, Oren D A, Peindl K S, Wisner K L. Randomized clinical trial of bright light therapy for antepartum depression: preliminary findings. J Clin Psychiatry. 2004 March; 65(3): 421-5.
28. Gallin P F, Terman M, Reine C E, Rafferty B, Terman J S, Burde R M. Opthalmologic examination of patients with seasonal affective disorder, before and after bright light therapy. Am J. Opthalmol. 1995 February; 119(2): 202-10
29. Oren D A, Wisner K L, Spinelli M, Epperson C N, Peindl K S, Terman J S, Terman M An open trial of morning light therapy for treatment of antepartum depression. Am J. Psychiatry. 2002 April; 159(4): 666-9. Am J. Psychiatry. 2002

30. Dennis C L, Stewart D E. Treatment of postpartum depression, part 1: a critical review of biological interventions. J Clin Psychiatry. 2004 September; 65(9): 1242-51
31. Praschak-Rieder N, Willeit M, Neumeister A, Hilger E, Stastny J, Thierry N, Lenzinger E, Kasper S. Prevalence of premenstrual dysphoric disorder in female patients with seasonal affective disorder. J Affect Disord. 2001 March; 63(1-3): 239-42.
32. Lam R W, Carter D, Misri S, Kuan A J, Yatham L N, Zis A P. A controlled study of light therapy in women with late luteal phase dysphoric disorder. Psychiatry Res. 1999 Jun. 30; 86(3): 185-92.
33. Kennedy S H, Lam R W, Cohen N L, Ravindran A V; CANMAT Depression Work Group. Clinical guidelines for the treatment of depressive disorders. IV. Medications and other biological treatments. Can J. Psychiatry. 2001 June; 46 Suppl 1:38 S-58S
34. Tam E M, Lam R W, Levitt A J. Treatment of seasonal affective disorder: a review Can J. Psychiatry. 1995 October; 40(8): 457-66.
35. Meesters Y, Beersma D G, Bouhuys A L, van den Hoofdakker R H. Prophylactic treatment of seasonal affective disorder (SAD) by using light visors: bright white or infrared light? Biol Psychiatry. 1999 Jul. 15; 46(2): 239-46
36. Blehar M C, Rosenthal N E. Seasonal affective disorders and phototherapy. Report of a National Institute of Mental Health-sponsored workshop. Arch Gen Psychiatry. 1989 May; 46(5): 469-74.
37. Avery D H, et al. Affect Disord. 2002 May; 69(1-3): 231-6
38. Avery D H, Eder D N, Bolte M A, Hellekson C J, Dunner D L, Vitiello M V, Prinz P N. Dawn simulation and bright light in the treatment of SAD: a controlled study. Biol Psychiatry. 2001 Aug. 1; 50(3): 205-16
39. Giedke H, et al. Sleep Med Rev. 2002 October; 6(5): 361-77
40. Praschak-Rieder N, Willeit M, Neumeister A, Hilger E, Kasper S. Therapeutic sleep deprivation and phototherapy Wien Med Wochenschr. 1999; 149(18): 520-4
41. Loving RT, et al. Depress Anxiety. 2002; 16(1): 1-3
42. Neumeister A, et al . . . Biol Psychiatry. 1996 Jan. 1; 39(1): 16-21
43. Cocilovo A. Colored light therapy: overview of its history, theory, recent developments and clinical applications combined with acupuncture. Am J. Acupunct. 1999; 27(1-2): 71-83
44. Wright HR et al., Differential effects of light wavelength in phase advancing the melatonin rhythm. J Pineal Res. 2004 March; 36(2): 140-4
45. Cajochen C., Munch M., Kobialka S., Krauki K., Steiner R., Oelhafen P., Orgul S., Wirz-Justice A. High sensitivity of human melatonin, alertness, thermoregulation and heart rate to short wavelength light. Clin Endocrinolog Metab. 2005; 90(3): 1311-6.
46. Glickman G. et al. Light Therapy for Seasonal Affective Disorder with Blue Narrow-Band Light-Emitting Diodes (LED's). Biol Psychiatry 2005 Sep. 13.
47. Wright H R, Lack L C, Partridge K J. Light emitting diodes can be used to phase delay the melatonin rhythm. J Pineal Res. 2001 November; 31(4): 350-5.
48. Benedetti F., Colombo C., Pontiggia A., Bernasconi A., Florita M., Smeraldi E. Morning light treatment hastens the antidepressant effect of citalopram: a placebo-controlled trial. J Clin Psychiatry. 2003 June; 64(6): 648-53.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art.

All references cited herein are incorporated herein by reference in their entirety and for all purposes to the same extent as if each individual publication, patent or patent application was specifically and individually indicated to be incorporated by reference in its entirety for all purposes. The citation of any publication is for its disclosure prior to the filing date and should not be construed as an admission that the present invention is not entitled to antedate such publication by virtue of prior invention.

What is claimed is:

1. A method of providing a multi-stage light protocol, the method comprising:
   operating a light source to emit at least broad spectrum white light during first, second and third stages of light emission such that, for a predetermined distance of about 45 cm from the light source:
   i. the first stage of light emission includes a simulated dawn process wherein the intensity of light gradually at the predetermined distance increases from substantially zero lux to between about 500 lux and about 1200 lux over a period of between about 20 minutes and about 90 minutes;
   ii. the second stage of light emission is subsequent to the first time window and includes a second time window of at least 90 minutes such that:
      A. for every 45 minute sub-window within the second time window, the light intensity at the predetermined distance, for a majority of the time of the sub-window, is equal to at least a second minimum value of at least about 500 lux;
      B. for a majority of the time of the second time window, the light intensity at the predetermined distance is equal to at most 2,000 lux; and
      C. for a majority of the time of the second window, light emitted from the light source comprises at least about 20% and at most about 60% colored light having a wavelength between 520 and 535 nm; and
   iii) the third stage of light emission is subsequent to the second time window and includes a third time window of at least 20 minutes such that, for a majority of the time of the third time window, the light intensity at the predetermined distance is equal to at least a high-intensity minimum value of at least about 5000 lux.

2. The method of claim 1 wherein said low-intensity minimum value is about 100 lux.

3. The method of claim 1 wherein said low-intensity minimum value is about 200 lux.

4. The method of claim 1 wherein said low-intensity minimum value is about 400 lux.

5. The method of claim 1 wherein said low-intensity maximum value is about 1500 lux.

6. The method of claim 1 wherein said low-intensity maximum value is about 1000 lux.

7. The method of claim 1 wherein a duration of said second time window is at least 120 minutes.

8. The method of claim 1 wherein said second minimum value is about 750 lux.

9. The method of claim 1 wherein said second minimum value is about 1000 lux.

10. The method of claim 1 wherein said second minimum value is about 1500 lux.

11. The method of claim 1 wherein the first, second and third stages are carried out such that an elapsed time between a beginning of said first time window and a beginning of said third time window is at most a maximum elapsed time value of 8 hours.

12. The method of claim 1 wherein the first, second and third stages are carried out such that an elapsed time between a beginning of said first time window and a beginning of said third time window is at most a maximum elapsed time value of 6 hours.

13. The method of claim 1, wherein said light source includes a plurality of LEDs, at least some said LEDS being white LEDS and at least some said LEDs being colored LEDS.

14. The method of claim 1 wherein a duration of said third time window is 40 minutes.

15. The method of claim 1 wherein a duration of said third time window is 60 minutes.

16. The method of claim 1 wherein a duration of said third time window is 75 minutes.

17. The method of claim 1 wherein said high-intensity minimum value is about 7500 lux.

18. The method of claim 1 wherein said high-intensity minimum value is about 9500 lux.

19. The method of claim 1 for treating at least one of a psychiatric disorder, a mood disorder, a circadian rhythm disorder, non-seasonal depression, binge eating, and seasonal depression.

20. Apparatus comprising:
   a) a light source configured to emit at least broad spectrum white light; and
   b) a controller pre-programmed to control the light source so as to carry out effect first, second and third stages of light emission such that, for a predetermined distance of about 45 cm from the light source:
      i. the first stage of light emission includes a simulated dawn process wherein the intensity of light gradually at the predetermined distance increases from substantially zero lux to between about 500 lux and about 1200 lux over a period of between about 20 minutes and about 90 minutes;
      ii. the second stage of light emission is subsequent to the first time window and includes a second time window of at least 90 minutes such that:
         A. for every 45 minute sub-window within the second time window, the light intensity at the predetermined distance, for a majority of the time of the sub-window, is equal to at least a second minimum value of at least about 500 lux;
         B. for a majority of the time of the second time window, the light intensity at the predetermined distance is equal to at most 2,000 lux; and
         C. for a majority of the time of the second window, light emitted from the light source comprises at least about 20% and at most about 60% colored light having a wavelength between 520 and 535 nm; and
      iii) the third stage of light emission is subsequent to the second time window and includes a third time window of at least 20 minutes such that, for a majority of the time of the third time window, the light intensity at the predetermined distance is equal to at least a high-intensity minimum value of at least about 5000 lux.

21. The apparatus of claim 20 wherein the controller is operative to carry out the simulated dawn process of so that the intensity of light gradually at the predetermined distance increases from substantially zero lux to between about 500 lux and about 1200 lux over a period of between about 30 minutes and about 75 minutes.

22. Apparatus as in claim 20 wherein said low-intensity minimum value is about 100 lux.

23. Apparatus as in claim 20 wherein said low-intensity minimum value is about 200 lux.

24. Apparatus as in claim 20 wherein said low-intensity minimum value is about 400 lux.

25. Apparatus as in claim 20 wherein said low-intensity maximum value is about 1500 lux.

26. Apparatus as in claim 20 wherein said low-intensity maximum value is about 1000 lux.

27. The apparatus as in claim 20 wherein said controller is pre-programmed such that a duration of said second time window is at least 120 minutes.

28. Apparatus as in claim 20 wherein said second minimum value is about 750 lux.

29. Apparatus as in claim 20 wherein said second minimum value is about 1000 lux.

30. Apparatus as in claim 20 wherein said second minimum value is about 1500 lux.

31. Apparatus as in claim 20 wherein said controller is pre-programmed to carry out said first, second and third stages such that an elapsed time between a beginning of said first time window and a beginning of said third time window is at most a maximum elapsed time value of 8 hours.

32. Apparatus as in claim 20 wherein said controller is operative to effect said first, second and third stages such that an elapsed time between a beginning of said first time window and a beginning of said third time window is at most a maximum elapsed time value of 6 hours.

33. Apparatus of claim 20, wherein said light source includes a plurality of LEDs, at least some said LEDS being white LEDS and at least some said LEDs being colored LEDS.

34. Apparatus as in claim 20 wherein said controller is configured such that a duration of said third time window is 40 minutes.

35. Apparatus as in claim 20 wherein said controller is configured such that a duration of said third time window is 60 minutes.

36. Apparatus as in claim 20 wherein said controller is configured such that a duration of said third time window is 75 minutes.

37. The apparatus of claim 20 wherein said high-intensity minimum value is about 7500 lux.

38. The apparatus of claim 20 wherein said high-intensity minimum value is about 9500 lux.

39. The method of claim 1 wherein the simulated dawn process of the first stage is carried out so that the intensity of light gradually at the predetermined distance increases from substantially zero lux to between about 500 lux and about 1200 lux over a period of between about 30 minutes and about 75 minutes.

* * * * *